United States Patent [19]

Pistorius

[11] Patent Number: 4,808,343
[45] Date of Patent: Feb. 28, 1989

[54] PROCESS FOR ISOLATING PARAFFINSULFONATES WITH A LOW ALKALI METAL SULFATE CONTENT AND SULFURIC ACID FROM PARAFFIN-SULFOXIDATION REACTION MIXTURES WITHOUT OBLIGATORY PRODUCTION OF SODIUM SULFATE

[75] Inventor: Rudolf Pistorius, Hünstetten, Fed. Rep. of Germany

[73] Assignee: Hoechst Aktiengesellschaft, Frankfurt am Main, Fed. Rep. of Germany

[21] Appl. No.: 120,859

[22] Filed: Nov. 16, 1987

[30] Foreign Application Priority Data

Nov. 18, 1986 [DE] Fed. Rep. of Germany ....... 3639464

[51] Int. Cl.$^4$ ........................................... C07C 143/02
[52] U.S. Cl. ................................................ 260/513 R
[58] Field of Search ....................... 260/513 R, 504 R

[56] References Cited

U.S. PATENT DOCUMENTS 4,177,208 12/1979 Boy et al. .
4,178,307 12/1979 Boy et al. .
4,557,873 12/1985 Pistorius .

FOREIGN PATENT DOCUMENTS 1532207 11/1978 United Kingdom .

Primary Examiner—Alan Siegel

[57] ABSTRACT

A process for isolating alkanesulfonates having a low alkali metal sulfate content and sulfuric acid from paraffin-sulfoxidation reaction mixtures with the aid of alcohols, the reaction mixture, freed from sulfur dioxide, being mixed in a sequence of five mixer/settler vessels with a $C_4$–$C_8$-alcohol and the amount of alkali metal hydroxide which is necessary for neutralization. The process is designed so that no alkali metal sulfate, but instead only sulfuric acid, is produced as a byproduct. Fewer alkali metal ions are thereby lost from the system, and the consumption of alkali metal hydroxide for neutralization is accordingly reduced.

3 Claims, 1 Drawing Sheet

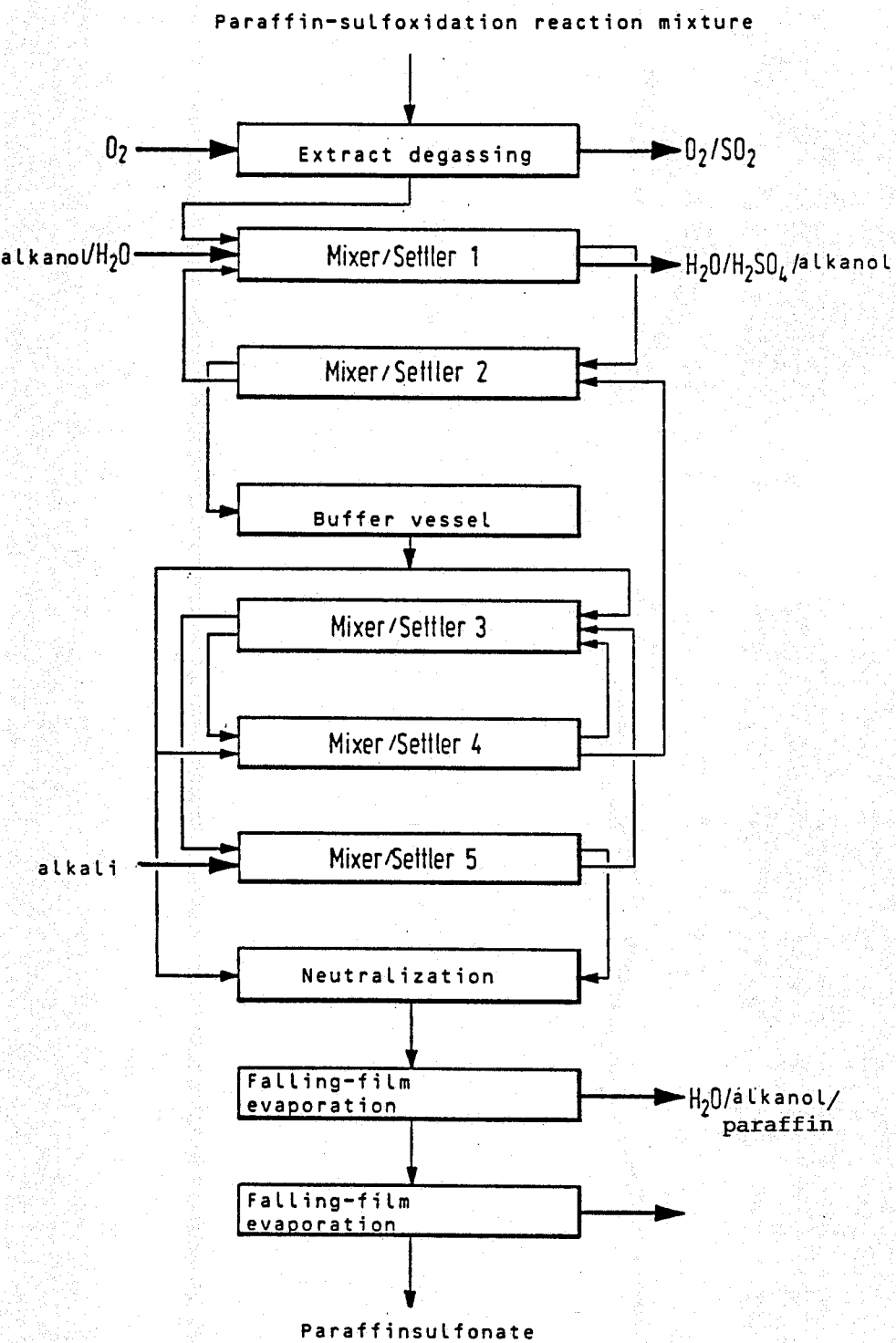

PROCESS FOR ISOLATING PARAFFINSULFONATES WITH A LOW ALKALI METAL SULFATE CONTENT AND SULFURIC ACID FROM PARAFFIN-SULFOXIDATION REACTION MIXTURES WITHOUT OBLIGATORY PRODUCTION OF SODIUM SULFATE

Process for isolating paraffinsulfonates with a low alkali metal sulfate content and sulfuric acid from paraffin-sulfoxidation reaction mixtures without obligatory production of sodium sulfate.

The aqueous solutions of paraffinsulfonic acids which are obtainable through sulfoxidation of n-paraffins, for example by the process of German Patent No. 910,165, additionally contain sulfur dioxide, sulfuric acid and hydrotropically dissolved paraffins. In order to isolate usable paraffinsulfonic acids or paraffinsulfonates of good quality, i.e. clear products which are as far as possible odor-free and have the lowest possible sulfuric acid and salt content, from such reaction mixtures, sulfur dioxide, sulfuric acid and paraffins must be removed as quantitatively and gently as possible. The paraffinsulfoxidation products already begin to decompose at temperatures above 50° C., which is outwardly apparent from discoloration of the acidic reaction mixture from waterclear via yellowish, brown and finally to a deep black. Even if the amount of paraffinsulfonic acid decomposed by the action of temperature is relatively low, so long as the acidic reaction mixtures are not subjected to temperatures above 100° C. for a relatively long period, even a small proportion of decomposed products requires a substantial amount of bleach, due to its color intensity, if perfectly clear products are desired.

It has been found that, in contrast, alkaline salts of paraffinsulfonic acids are relatively stable. Even in the case of relatively long heating, temperatures of below 200° C. lead only to very insubstantial discoloration, which can easily be eliminated again using small amounts of bleach.

It must therefore be ensured, from the very first step of work-up of the paraffin-sulfoxidation reaction mixtures, i.e. during degassing in order to remove sulfur dioxide, that discoloration does not occur if possible. If degassing is carried out in a slight vacuum, only very brief warming to about 85° C. is required in order to eliminate virtually all the sulfur dioxide. Blowing-out using inert gas or pure oxygen in a column filled with a suitable packing at a temperature of about 40°-85° C. is likewise possible.

Through immediately subsequent recooling of the reaction mixture to room temperature, noticeable decomposition, i.e. deepening of the color of the reaction mixture, can be prevented in this process step.

With respect to the quality of the paraffinsulfonate, it would be favorable to neutralize the reaction mixture immediately after degassing. However, such a procedure is uneconomic and technically complicated due to the high consumption of alkali necessary for neutralization of the sulfuric acid and due to the considerable losses of paraffinsulfonate which occur when filtering off the alkali metal sulfate.

After removal of the sulfur dioxide from the reaction mixture, it must therefore be attempted to remove the sulfuric acid from the mixture as completely as possible before neutralization while preserving the paraffinsulfonic acid. In known processes which have such an aim, a procedure is generally followed in which the degassed sulfoxidation mixture is treated with a suitable organic solvent in order to cause separation into an organic phase which contains the paraffinsulfonic acids, and an aqueous phase which contains the sulfuric acid, as far as possible in the form of a, generally, 10 to 25% strength aqueous solution. The two phases are then separated and the organic phase is further worked up in order to isolate the paraffin-sulfonic acids or their salts. Thus, it has already been disclosed in German Patent Application F No. 3,718,120, published on 29.1.1953, that water-insoluble or only sparingly water-miscible organic solvents, such as, for example, benzene, chlorobenzene, cyclohexane, carbon tetrachloride, chloroform, methylene chloride and the like, are added to the sulfoxidation mixture in order to separate sulfuric acid. Ethers, such as, for example, diethyl ether or di-n-butyl ether, are also used for the same purpose according to German Offenlegungsschrift No. 2,730,245, and ketones or esters according to German Offenlegungsschrift No. 2,745,691 and alcohols having at least 5 carbon atoms according to German Offenlegungsschrift No. 2,139,477.

None of these known processes for removal of sulfuric acid at low temperatures has hitherto been able to establish itself on a large industrial scale since either the expense for distillative work-up of the product solution is too high and/or the degree of removal of sulfuric acid from the reaction mixture is inadequate to finally obtain low-salt products which contain less than 2% by weight of residual salt (relative to 100% of paraffinsulfonate).

Thus, for example using alcohols having 4 to 6 carbon atoms in a one-step extraction, it is only possible to remove the sulfuric acid so incompletely that the salt content in the neutralized final product is still considerably above 2% by weight (relative to paraffinsulfonate), even if the amount of alcohol added is increased to 30% by weight (relative to the degassed sulfoxidation reaction mixture). In contrast, larger or smaller amounts of alcohol lead to even less complete removal of sulfuric acid.

However, if water is again added, for example after removal using hexanol, in order to extract further sulfuric acid from the reaction mixture (2-step extraction) so that the residual salt content in the paraffinsulfonate does not finally exceed 2% by weight (again relative to the wash-active substance), it can be seen that not inconsiderable amounts of water are necessary for this and they only separate out again to a small extent, which very greatly increases the distillative cost.

On the one hand, the degree of sulfuric acid removal increases with increasing C number of the alcohols employed, but on the other hand the work-up expense becomes greater as the boiling points of the alcohols used rise.

German Offenlegungsschrift No. 3,342,984 likewise describes a process for isolation of paraffinsulfonates with a low alkali metal sulfate content and sulfuric acid from paraffin-sulfoxidation reaction mixtures with the aid of alcohols.

The starting point here is the reaction mixture obtained on sulfoxidation of n-paraffins, in particular $C_{13}$–$C_{18}$ paraffins, which is freed from sulfur dioxide by degassing and which is stirred at temperatures from 15° to 80° C., in particular 25° to 35° C., with 15 to 30, in particular 17 to 25, % by weight of a $C_4$–$C_8$-alcohol. Isobutanol is preferred in this process.

This alkanesulfonic acid/alcohol solution is introduced continuously to an apparatus which comprises three combined mixer/settler vessels and a further mixer vessel.

The paraffinsulfonic acid/alcohol solution, the upper phase of the 2nd settler and the lower phase of the 3rd settler are fed into the 1st mixer, and the lower phase of the 1st settler and sufficient of the alkanesulfonic acid/alcohol solution so that the pH in the 2nd mixer/settler is always between 7 and 8 are fed into the 2nd mixer. The 3rd mixer accommodates all the alkali metal hydroxide solution required and the product phase from the 1st settler. The lower phase from the 2nd settler, comprising an aqueous alkali metal sulfate solution containing a trace of alcohol (less than 1% by weight), and the upper phase from the 3rd settler, which is adjusted to a pH of about 11 in the mixer vessel using further alkanesulfonic acid/alcohol solution, are discharged. This solution is then evaporated to the desired degree of concentration.

A critical disadvantage in this procedure is the obligatory production of aqueous alkali metal sulfate solutions, which are, in addition, contaminated by traces of the alcohol used. Due to the great tendency of these solutions towards foaming, these traces of alcohol can scarcely be removed by distillation. Before such waste water can be fed to biological clarification plants, the sulfate, which destroys concrete walls, must normally also be removed, which involves further disposal problems.

It has now been found that these disadvantages of the known process can be avoided if a further mixer/settler vessel is introduced and the aqueous alkali metal sulfate solutions are reintroduced into the circuit via this vessel. The invention therefore relates to a process for isolating alkanesulfonates having a low alkali metal sulfate content and sulfuric acid from paraffin-sulfoxidation reaction mixtures with the aid of alcohols, in which process the reaction mixture, freed from sulfur dioxide, is mixed in a mixer/settler vessel (1) with a $C_4$–$C_8$-alcohol and the lower phase from a mixer/settler vessel (2), the dilute sulfuric acid lower phase which separates out is removed, the upper product phase remaining is transferred, together with the lower phase from a mixer/settler vessel (4), into mixer/settler vessel (2), the lower phase obtained in the latter is transferred into mixer/settler vessel (1), the remaining upper product phase (2) from mixer/settler vessel (2), together with the lower phase from a mixer/settler vessel (5) and the upper phase from mixer/settler vessel (4) are transferred into a mixer/settler vessel (3), the upper phase obtained in mixer/settler vessel (3), together with the amount of alkali metal hydroxide which is necessary for neutralization, is transferred into mixer/settler vessel (5), the lower phase obtained in mixer/settler vessel (3) is transferred into mixer/settler vessel (4) at the same time as an amount of the product phase (2) such that a pH of 0.5 to 7 is maintained in the latter vessel, the upper phase obtained in settler vessel (4) is transferred into mixer/settler vessel (3), the lower phase obtained in mixer/settler vessel (4) is transferred into mixer/settler vessel (2), the lower phase obtained in mixer/settler vessel (5), together with the product phase (2), is transferred into mixer/settler vessel (3), and the upper phase obtained in mixer/settler vessel (5) is adjusted to a pH of 3 to 9 by adding part of the product phase (2) and concentrated by evaporation.

This process is illustrated in greater detail with reference to the schematic drawing which is appended.

BRIEF DESCRIPTION OF THE DRAWING

The drawing is a flow sheet schematically illustrating the sequence and interrelationship of process steps of a preferred embodiment of this invention.

The reaction mixture from the sulfoxidation, freed from $SO_2$ and having the approximate composition:
39–41% of $H_2O$
7–8% of $H_2SO_4$
20–23% of $RSO_3H$, R=$C_{13}$–$C_{17}$ n-paraffin mixture
30–32% of paraffin
is introduced into a mixer/settler 1 into which the lower phase from a mixer/settler 2, comprising an approximately 8–14% strength sulfuric acid with about 2–7% of sodium hydrogen sulfate, is simultaneously running.

At the same time, sufficient water-saturated alkanol (15–40%, depending on the carbon chain length of the alkanol used, about 18–40%, in particular 21–30%, in the case of isobutanol, which is preferred, relative to the amount of the degassed extract) is pumped into mixer 1 so that an approximately 15–20% strength sulfuric acid is separated off in settler 1 as the lower phase, which is contaminated with, at most, low amounts of alkali metal hydrogen sulfate (for example <1.5% of $NaHSO_4$, relative to the approximately 80% strength sulfuric acid evaporated) and can easily be evaporated to 78–80% without the subsequent alkali metal hydrogen sulfate crystallizing out.

The amount of alkanol added at this point influences the alkali metal sulfate content in the final product, i.e. in the paraffinsulfonate melt, to be precise such that the residual salt content decreases as the amount of alkanol increases. However, an alkanol proportion of greater than 35% leads only to an insignificant decrease in this content in the melt.

The upper phase from settler 1 is mixed in mixer 2 by stirring with the lower phase from settler 4, which essentially comprises an approximately 3–10% strength aqeuous alkali metal hydrogen sulfate solution when the alkanol used is isobutanol. The upper phase then separated off in settler 2 flows into a buffer vessel from which sufficient of each of an alkanolic and paraffin-containing alkanesulfonic acid solution is pumped into mixer 4 so that a pH between 0.5 and 7, preferably 1–5, but in particular 1–1.5, is produced in the latter.

The remaining alkanesulfonic acid solution, which makes up about ⅔ of the total stream and flows through the buffer vessel, is mixed in a mixer 3 with the upper phase from settler 4, comprising acidic, alkanolic alkanesulsulfonate solution, and the lower phase from settler 5, comprising an aqueous alkali/alkali metal sulfate solution (for example about 1–5% of $Na_2SO_4$ and about 10–40% of NaOH in the case of isobutanol, which is preferred).

The lower phase from settler 3, likewise an alkaline alkali metal sulfate solution (which can contain, for example, 6–10% of $Na_2SO_4$ and 0.5–8% of NaOH) runs into mixer 4, while the upper phase from settler 3, an alkaline alkanesulfonate solution, is treated in mixer 5 with the amount of sodium hydroxide solution which is necessary for neutralization of all the alkanesulfonic acid.

The alkaline upper phase from settler 5 flows to neutralization, where it is adjusted to a pH of 3 to 9, preferably 5 to 8, using part of the sulfonic acid solution from the buffer vessel.

This neutralizate is finally evaporated to a melt in two falling-film evaporators connected together. In the first falling-film evaporator (heating jacket steam pressure about 3–6 bar), the major part of the water and the isobutanol distill off at atmospheric pressure. In the second falling-film evaporator, which is operated at a heating mantle steam pressure of 20–30 bar, in particular about 22–26 bar, in a vacuum of 15–30 mbar, in particular 17–19 mbar, the paraffin evaporates together with the remaining amounts of water and isobutanol.

About 97–98% of the paraffinsulfonate melt thus obtained is alkanesulfonate, 0.8–1.3% is paraffin and 1.0–1.7% is $Na_2SO_4$.

Mixer/settlers 1 and 2 are operated at temperatures of 12° to 80° C., preferably 25°–50° C., in particular 30°–35° C. For optimum phase separation, mixer/settlers 3 and 5 should be operated as close as possible to the boiling point of the mixture, for example, 88°–91° C. at atmospheric pressure when the alkanol is isobutanol. Not quite so well, but still adequately well and becoming better with increasing temperature, the phase separation with isobutanol as the alkanol also proceeds adequately quickly and completely at 40°–88° C.. The mixer/settler 4 can also be operated at temperatures of 40°–80° C. but also at temperatures up to 91° C., a temperature of 60°–85° C., in particular 70° C., being ideal.

In an analogous fashion, the higher $C_5$–$C_8$-alkanols can, of course, also be employed and have the advantage that the residual sulfate content in the final product can be further reduced slightly with increasing carbon chain length of the alkanol. However, it is a disadvantage here that the energy consumption for separation of water and alkanol on the one hand and alkanol and paraffin on the other hand increases very rapidly.

Suitable alkalization agents, besides NaOH, are also potassium hydroxide solution or other bases such as, for example, MgO or $Mg(OH)_2$, ZnO or mixtures thereof.

The advantages of this process are that no alkali metal sulfate, but instead only sulfuric acid, is produced as a waste product. Fewer alkali metal ions are thereby lost over the entire process. This has the consequence that the amount of alkali metal hydroxide which is required for neutralization is reduced. It is additionally of advantage that, compared to the previously known process, the content of alcohols in the waste water removed by distillation is very much lower.

EXAMPLE 27 kg of a sulfoxidation reaction mixture of the following composition
40% of water
7.5% of sulfuric acid
21.5% of $RSO_3H$, $R=C_{13}$–$C_{17}$-alkyl,
31% of paraffin
are introduced into a mixer/settler 1 into which the lower phase from a mixer/settler 2, comprising 10% strength sulfuric acid containing about 4% of sodium hydrogen sulfate, is running simultaneously. At the same time, 23%, relative to the amount of sulfoxidation in the reaction mixture, of water-saturated isobutanol are pumped into the mixer 1. During this, a 17% strength sulfuric acid further containing about 1% of sodium hydrogen sulfate, relative to evaporated 80% strength sulfuric acid, separates out as the lower phase in settler 1. This sulfuric acid is removed from the overall circuit and concentrated by evaporation. The upper phase from settler 1 is stirred into mixer 2 with the lower phase from a settler 4, which essentially comprises an approximately 6% strength sodium hydrogen sulfate solution. The upper phase subsequently separated off in settler 2 then flows into a buffer vessel from which in each case sufficient is pumped into mixer 4 so that a pH of 1 is produced in the latter. The remaining alkanesulfonic acid solution from the buffer vessel, which makes up about ⅞ of the entire stream which flows through the buffer vessel, is mixed in a mixer 3 with the upper phase from settler 4, comprising an acidic, isobutanolic alkanesulfonate solution and, with the lower phase from settler 5, comprising an aqueous solution containing 14% of NaOH and 3.5% of $Na_2SO_4$.

The lower phase from settler 3, likewise an alkaline sodium sulfate solution containing 2.7% of NaOH and 8% of $Na_2SO_4$, runs into mixer 4, while the upper phase from settler 3, an alkaline alkanesulfonate solution, is mixed in mixer 5 with the amount of sodium hydroxide solution which is necessary for neutralization of all the alkanesulfonic acid. The amount is about 2.0 kg of NaOH (50% strength). The alkaline upper phase from settler 5 flows into the neutralization stage, where it is adjusted to pH 7 using part of the sulfonic acid solution from the buffer vessel.

This neutralizate is finally evaporated to a melt in two falling-film evaporators connected together. In the first falling-film evaporator (heating mantle steam pressure about 4 bar), the major part of the water and the isobutanol distill off at atmospheric pressure. In the second falling-film evaporator, which is operated at a heating mantle steam pressure of 24 bar in a vacuum of 18 mbar, the paraffin evaporates together with the remaining amounts of water and isobutanol.

97.5% of the alkanesulfonate melt thus obtained is Na alkanesulfonate, 1% is paraffin and 1.5% is sodium sulfate.

Mixer/settlers 1 and 2 are operated at 34° C., mixer/settlers 3 and 5 at 90° C. and mixer/settler 4 at 75° C.

I claim:

1. A process for isolating alkanesulfonates having a low alkali metal sulfate content and sulfuric acid from paraffinsulfoxidation reaction mixtures with the aid of alcohols, wherein the reaction mixture, freed from sulfur dioxide, is mixed in a mixer/settler vessel (reference numeral 1 of the Drawing) with a $C_4$–$C_8$-alcohol and the lower phase from a mixer/settler vessel (reference number 2 of the Drawing), the dilute sulfuric acid lower phase which separates out is removed, the upper product phase remaining is transferred, together with the lower phase from a mixer/settler vessel (reference numeral 4 of the Drawing), into mixer/settler vessel (reference number 2 of the Drawing), the lower phase obtained in the latter is transferred into mixer/settler vessel (reference numeral 1 of the Drawing), the remaining upper product phase from mixer/settler vessel (reference numeral 2 of the Drawing), together with the lower phase from a mixer/settler vessel (reference numeral 5 of the Drawing) and the upper phase from said mixer/settler vessel (4) are transferred into a mixer/settler vessel (reference numeral 3 of the Drawing), the upper phase obtained in said mixer/settler vessel (3), together with the amount of alkali metal hydroxide which is necessary for neutralization, is transferred into said mixer/settler vessel (5), the lower phase obtained in said mixer/settler vessel (3) is transferred into said mixer/settler vessel (4) at the same time as an amount of the product phase (reference numeral 2 of the Drawing)

such that a pH of 0.5 to 7 is maintained in the latter vessel, the lower phase obtained in the said settler vessel (4) is transferred into said mixer/settler vessel (2), the lower phase obtained in said mixer/settler vessel (5), together with the said product phase (2), is transferred into said mixer/settler vessel (3), and the upper phase obtained in said mixer/settler vessel (5), is adjusted to a pH of 3 to 9 by adding part of the said product (2) and concentrated by evaporation to recover the alkanesulfonate.

2. The process as claimed in claim 1, wherein a pH of 1 to 5 is maintained in said mixer/settler vessel (4).

3. The process as claimed in claim 1, wherein the alkanesulfonate which is recovered from the concentrated produce phase is about 97–98% pure.

* * * * *